United States Patent [19]

Latina

[11] Patent Number: 5,522,837
[45] Date of Patent: Jun. 4, 1996

[54] NASOLACRIMAL DUCT OCCLUSION DEVICE AND METHOD

[76] Inventor: Mark A. Latina, 71 Paddock La., North Andover, Mass. 01845

[21] Appl. No.: 262,002

[22] Filed: Jun. 17, 1994

Related U.S. Application Data

[63] Continuation-in-part of Ser. No. 816,376, Dec. 27, 1991, abandoned.

[51] Int. Cl.⁶ ............................ A61B 17/122; A61F 5/08
[52] U.S. Cl. ................................. 606/201; 606/204.45
[58] Field of Search ......................... 606/204.45, 858, 606/151, 157, 201, 204; 24/532, 555

[56] References Cited

U.S. PATENT DOCUMENTS

| 299,168 | 12/1988 | Bergstrom et al. | D24/27 |
|---|---|---|---|
| 580,954 | 4/1897 | Ray | 606/157 |
| 2,015,617 | 9/1935 | Claudius | 128/346 |
| 2,064,986 | 2/1936 | Mezz | 128/346 |
| 2,488,616 | 11/1949 | Browne | 606/157 |
| 2,620,793 | 12/1952 | Gollubier | 128/858 |
| 2,681,652 | 6/1954 | Laxton | 128/858 |
| 2,757,665 | 8/1956 | Tanikawa | 128/76 |
| 3,115,360 | 12/1961 | Witkoff | 294/99 |
| 3,349,771 | 10/1967 | Baer | 128/325 |
| 3,463,157 | 8/1969 | Hunt | 128/325 |
| 3,579,751 | 5/1971 | Jonckheere | 128/346 |
| 3,616,497 | 11/1971 | Esposito, Jr. | 24/81 |
| 3,802,437 | 4/1974 | Kees, Jr. | 128/325 |
| 4,033,342 | 7/1977 | Lake | 128/140 |
| 4,269,190 | 5/1981 | Behney | 128/325 |
| 4,445,508 | 5/1984 | Lake | 128/201 |
| 4,457,756 | 7/1984 | Kern et al. | 604/286 |
| 4,915,684 | 4/1990 | MacKeen et al. | 604/8 |
| 4,959,048 | 9/1990 | Seder et al. | 604/9 |

FOREIGN PATENT DOCUMENTS

| 3302707 | 12/1983 | Germany . |
|---|---|---|
| 8501650 | 4/1985 | Germany . |
| 1174005 | 8/1985 | U.S.S.R. . |

*Primary Examiner*—Carlos A. Azpuru
*Attorney, Agent, or Firm*—Lahive & Cockfield

[57] ABSTRACT

A method and device for nasolacrimal duct occlusion during eye medication provides a device having a pair of joined legs terminating in angled elements for fitting into the medial canthal area and compressing the nasolacrimal ducts. The device is placed over the nasal bridge during, and for a short time after, eye medication.

8 Claims, 3 Drawing Sheets

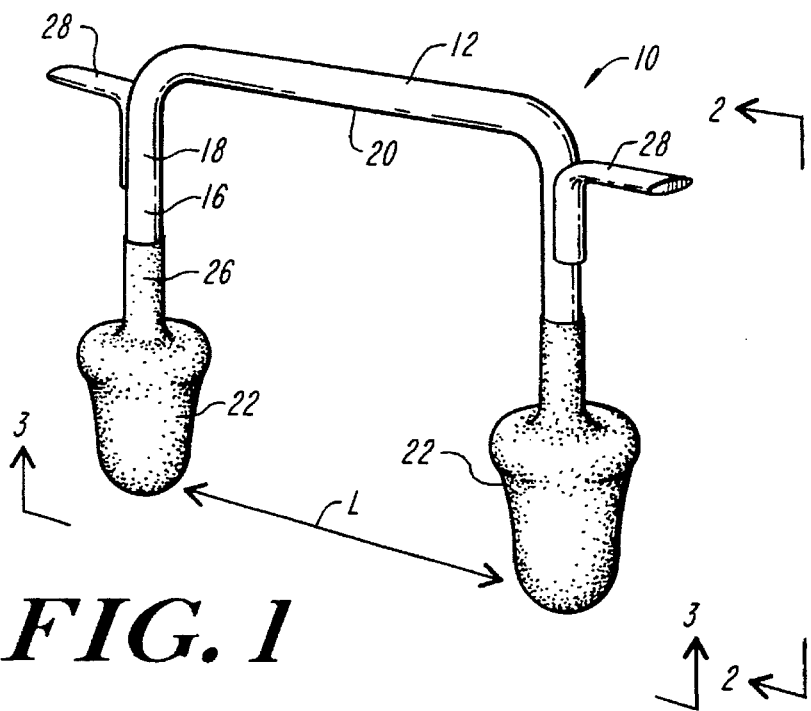
FIG. 1
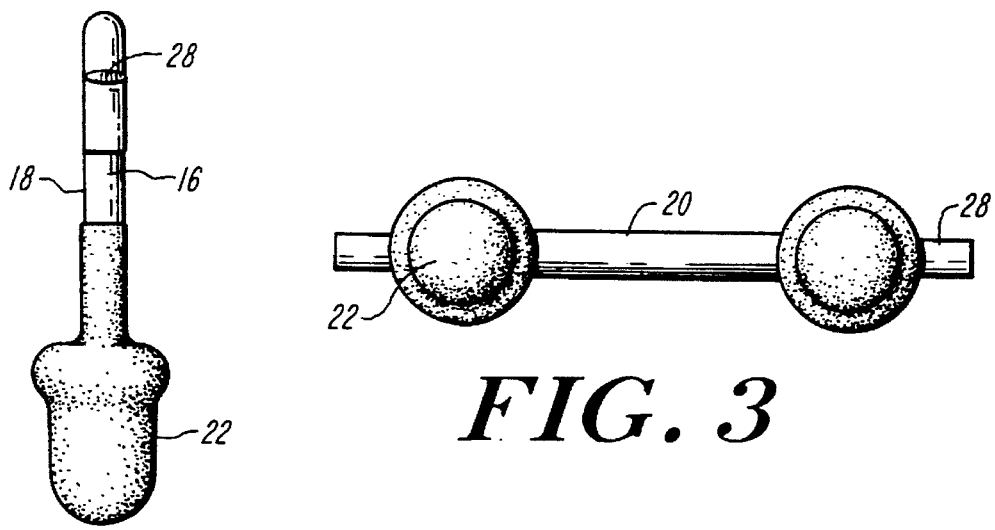
FIG. 2
FIG. 3
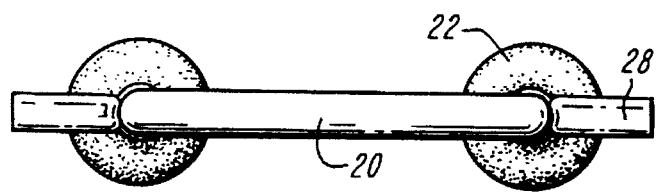
FIG. 4

NASOLACRIMAL DUCT OCCLUSION DEVICE AND METHOD

This application is a continuation-in-part of application Ser. No. 07/816,376 filed Dec. 27, 1991 now abandoned.

The invention relates to the occlusion of nasolacrimal ducts during eye medication, and particularly to devices and methods for such occlusion.

Systemic absorption of ocular medication (eye drops) through the nasal mucosa is well known. A variety of ocular medications, especially anti-glaucoma medications, are systemically absorbed following topical installation of the eye drops. For the Beta-blockers systemic absorption is sufficient to cause significant adverse effects such as asthma and cardiac problems in sensitive patients. Furthermore, it has been shown that the effectiveness of topical eye medications can be improved by manual punctal, or nasolacrimal, occlusion for a period of approximately two minutes. Thus the concentration of ocular medication can be reduced, i.e., Pilocarpine 2% instead of Pilocarpine 4%, yet be as effective as the higher dose.

While nasolacrimal occlusion can be performed by the patient by placing his or her fingers over the medial canthus and pressing over the nasolacrimal duct, patients, especially the elderly, usually cannot perform the task properly enough to result in an effective occlusion. The purpose of the invention is to provide a device and a method for reliably and effectively occluding the nasolacrimal ducts during topical eye medication.

SUMMARY OF THE INVENTION

The invention provides a method for avoiding absorption of topical eye medication through the nasal mucosa, of (a) providing a device adapted to occlude the nasolacrimal ducts, the device having a pair of bulbous elements formed to fit into the medial canthal area and compress the nasolacrimal ducts of the eyes, and a joined pair of leg elements extendible down each side of the nose, one of the bulbous elements mounted on the end of each leg element, the joined pair of leg elements being biased to press the bulbous elements into the medical canthal area, (b) placing the device in the region of the nasal bridge to occlude the nasolacrimal ducts during the application of eye medication and for a short period of time, preferably about two minutes, afterwards, and (c) removing the device.

The device of the invention includes a pair of bulbous elements formed to fit into medial canthal area and compress the nasolacrimal ducts of the eyes, a joined pair of leg elements extendible down each side of the nose, with a bulbous element mounted on the end of each leg element, and the bulbous elements being spaced apart a distance approximately equal to the distance between adjoining medial canthal areas. In preferred embodiments, the leg elements are made of a hard core with a coating of soft material, further include tubular elements mounted on the leg elements with an entrance for eye medication and an exit for application of the eye medication to the eye at a predetermined location, and still further include eyeglass-like temples mounted on the leg elements for securing the joined pair of leg elements to the ears of a user.

In one preferred embodiment, the device includes contact surfaces at one end of a pair of leg elements, the contact surfaces being at angles to the forward axis of the nose, corresponding to the angular relationship of the nasolacrimal ducts to the forward axis. The device also includes cross piece means for joining the other end of the leg elements, and handles extending from opposite ends of the cross piece, the device being elastic enough so that squeezing the handles spreads apart the contact surfaces.

DESCRIPTION OF THE DRAWINGS

Other objects, features and advantages of the invention will be described in, or will be inherent in, the following description of preferred embodiments of the invention, including the drawings thereof, in which:

FIG. 1 is a perspective view of a first embodiment of a device constructed according to the invention;

FIG. 2 is an end view of the device of FIG. 1, along the line 2—2;

FIG. 3 is a bottom view of the device of FIG. 1, along the line 3—3;

FIG. 4 is a top view of the device of FIG. 1;

BRIEF DESCRIPTION OF THE PREFERRED EMBODIMENTS

Figure 5:
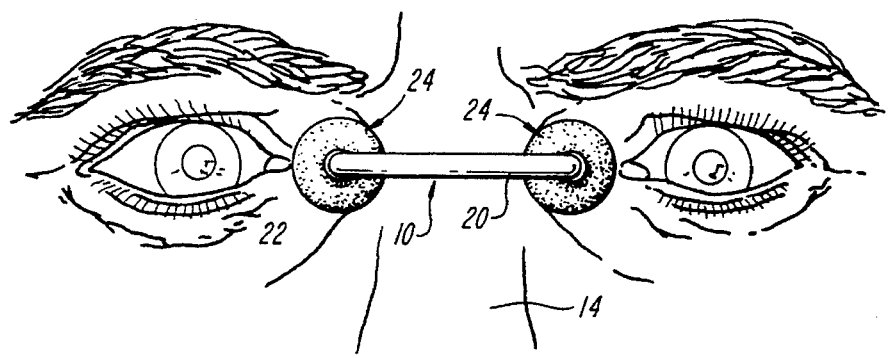
FIG. 5 is a perspective view of a patient with the device applied.

FIGS. 1, 2, 3 and 4 are different views of a first device 10 constructed according to the invention. The device 10 shown, in this first preferred embodiment, has a metal or plastic core 12 to provide structural support for the device, with a coating of soft material such as non-toxic rubber 16 or plastic polymer. The device could be made of a plastic material structure, with a central core of plastic which is harder, surrounded by a softer plastic or rubber material.

The device has a pair of legs 18 joined by a cross piece 20, the legs being selected to have adequate length, and being wide enough apart, to extend down both sides of the nasal bridge 14.

At the ends of the legs are two bulbous elements 22, or pontoons, which will fit into the medial canthal area 24 to compress the nasolacrimal ducts of the eyes. The bulbous elements 22 are spaced apart a distance, L, approximately equal to the distance between adjoining medical canthal areas 24. That is, they are spaced apart so that when pressed down on the bridge of the nose, the bulbous elements 22 which are of a soft compressible material, will compress the nasolacrimal ducts.

The bulbous elements 22 may be dip-coated vinyl 26 or dip-coated latex or can be covered with a soft foam or rubber-like material, to provide a comfortable feel for the patient.

In use (see FIG. 5), the device 10 is pressed down on the nasal bridge 14. The device 10 is held in place during the application of eye medication, such as eye drops, and for a short time afterward. The time is whatever is reasonable for the effect of the eye medication; a typical time is two minutes. Then the device 10 is removed.

The device 10 includes tabs 28 fixed to the legs 18 and projecting outwardly. The tabs 28 allow the device to be grasped by the fingers to apply pressure to the device to compress the nasolacrimal ducts.

Figure 6:
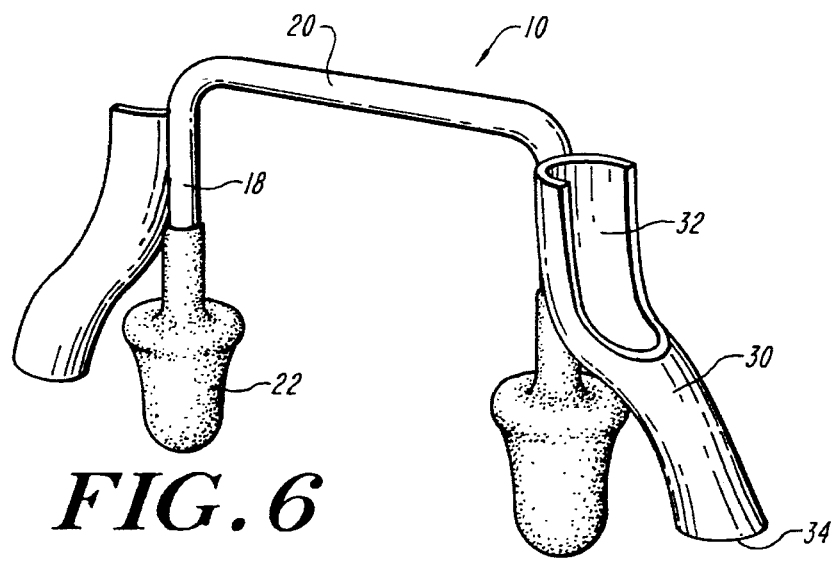
FIG. 6 is a perspective view of a second embodiment of the invention.

FIG. 6 shows a variation of device 10 which includes channels 30 for the application of eye drops. The channels 30 are tubular elements with a widened open top 32 into which eye drops may be placed, and exit ends 34 located so that the exiting eye drops flow properly into the eye, while the device 10 is in place.

Figure 7:
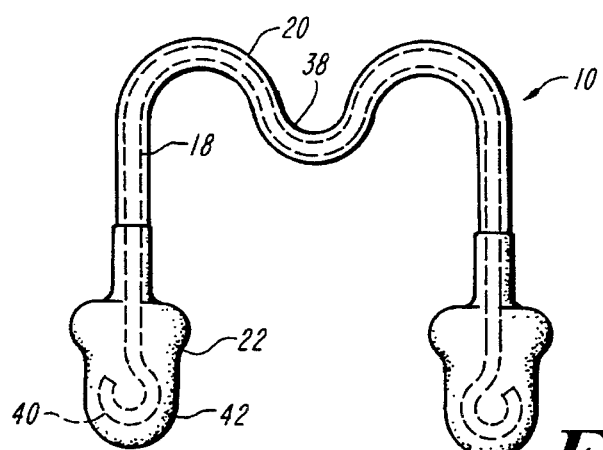
FIG. 7 is a front view of a third embodiment.

FIG. 7 shows another embodiment of the device with a metal core 36 having an inward curve 38 at the cross piece into which a finger can be placed when using the device. In the embodiment shown in FIG. 7 the bottoms of the legs are curved metal ends 40 about which silicon or rubber material 42 is placed to form bulbous elements 22.

Figure 8:
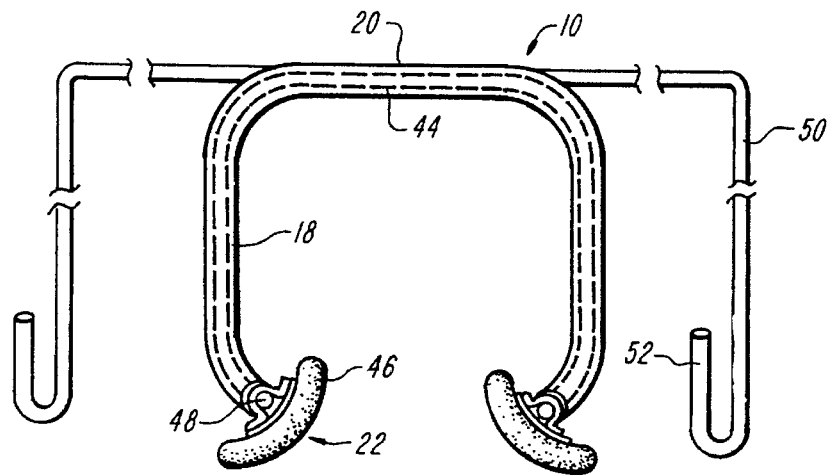
FIG. 8 is a front view of a fourth embodiment.

FIG. 8 shows still another embodiment of the invention, in which a hard plastic core 44 ends with bulbous elements 22 shaped like thick eyeglass nose pieces 46 pivotable about pins 48 at the end of legs 18. FIG. 8 also shows, diagrammatically, the addition of eyeglass-like temples 50 to the device 10, that have traditionally shaped curved ends 52 to engage the ears, so that a user does not have to hold the device in position after it is put in place.

Figure 9:
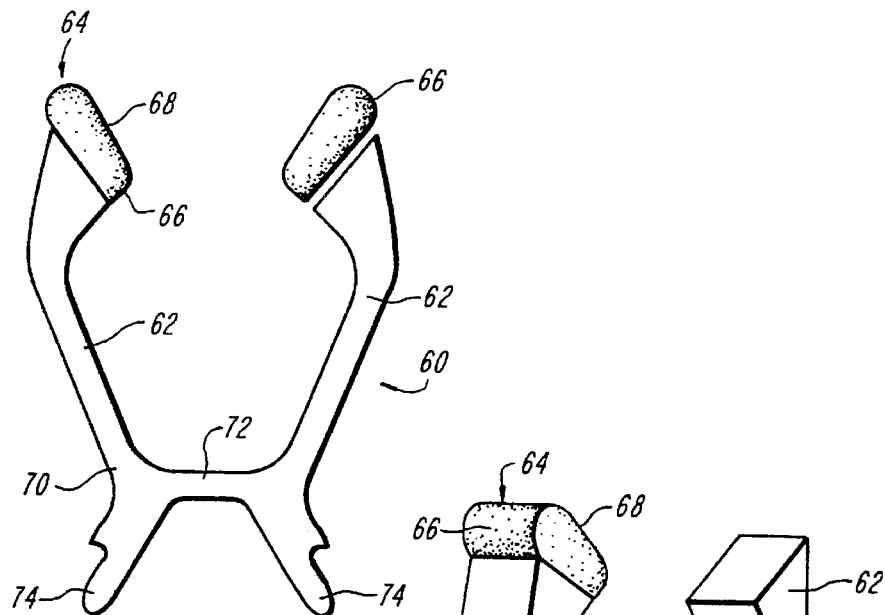
FIG. 9 is a front view of a fifth embodiment.
Figure 10:
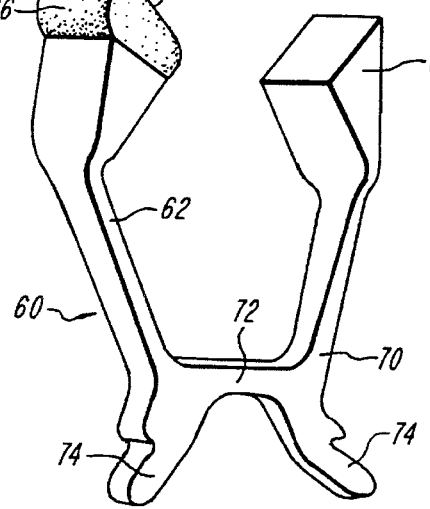
FIG. 10 is a perspective view of the fifth embodiment.

FIGS. 9 and 10 show another embodiment of the invention, designed to meet even more specifically the anatomic requirements for providing appropriate and adequate occlusion of the nasolacrimal ducts. The nasolacrimal ducts are located anatomically at the inner canthus of the eye lids and are directed inferiorly into the base of the nose into the middle turbinate of the nose. The anatomic region of the nose at its base, where the nasolacrimal duct travels, at the inner canthus of the eyelids, is at an angle to the forward axis of the nose (in FIG. 5, a line extending perpendicularly up from the drawing).

As shown in FIGS. 9 and 10, the fifth embodiment shows a frame 60 made from semi-rigid plastic. The frame 60 includes two legs 62 extendible down each side of the nose. The legs 62 are angled out and then in, terminating in ends 64 that are approximately equal to the distance between adjoining medial canthal areas of the nose of the user.

The ends 64 of the legs 62 are pads 66 of a firm but elastically deformable, material, such as rubber, plastic and the like. The deformability is to allow some comfort to the user and some conformability to the shape of the nose. The material is firm, however, to carry out the basic goal of pressure on the nasolacrimal ducts. FIG. 9 shows one of the pads 66 as a separate piece spaced apart from one of the legs 62, and shows another pad 66 attached to the other leg 62, to demonstrate that the pads 66 are separate. FIG. 10 shows one of the legs 62 with no pad 66 attached. The pads 66 need not be separate, of course, and can be formed from the very ends of the frame legs 62 if the material of the frame 60 is suitable.

The pads 66 at the ends 64 of the legs 62 have contact surfaces 68 to fit into the medial canthal area and compress the nasolacrimal ducts of the eyes. The contact surfaces 66, substantially planar, are at an angle to the forwards axis of the nose, corresponding to the angular relationship of the nasolacrimal ducts to the forward axis of the nose.

At the other ends 70 of the legs 62, the frame 60 includes a cross piece 72 joining the legs 62. The cross piece 72 provides a way to grasp the device and to press the device down on the nasolacrimal ducts. The cross piece 72 has two handles 74 extending from opposite ends. The material making up the frame 60 is selected to be sufficiently elastic that squeezing together the handles 74 will spread apart the duct contact surfaces 68 at the ends of the legs 62 to position the device over the ducts, and then releasing the handles 74 will provide some lateral and inferior compression of the nasolacrimal ducts.

Other variations of the device are conceivable. All of these are within the ability of those skilled in the art and are intended to be covered by the following claims.

I claim:

1. A device for occluding the nasolacrimal ducts, comprising, a pair of contact elements formed to fit into the medial canthal area and compress the nasolacrimal ducts of the eyes, a pair of leg elements extendible down each side of the nose, one of said contact elements mounted on the end of each leg element, said contact elements being spaced apart a distance approximately equal to the distance between adjoining medial canthal areas of the user and cross piece means for joining said pair of leg elements, said cross piece means including means for pressing said device down to compress the nasolacrimal ducts.

2. The device of claim 1 wherein said leg elements comprise a hard core with a coating of soft material.

3. The device of claim 1 further including tubular elements mounted on said leg elements, having an entrance for eye medication and an exit for application of the eye medication to the eye at a predetermined location.

4. The device of claim 1 further including temple elements mounted on said leg elements, for securing said joined pair of leg elements to the ears of a user.

5. The device of claim 1 wherein each of said pair of bulbous elements form a contact surface for contacting said medial canthal area, said contact surface oriented to maximize occlusion of the nasolacrimal ducts.

6. A device for occluding the nasolacrimal ducts, comprising, a pair of leg elements extendible down each side of the nose, one end of each of said leg elements forming a contact surface formed to fit into the medial canthal area and compress the nasolacrimal ducts of the eyes, said contact surfaces being at angles to the forward axis of the nose corresponding to the angular relationship of the nasolacrimal ducts to the forward axis of the nose, said contact surfaces being spaced apart a distance approximately equal to the distance between adjoining medial canthal areas of the nose, and cross piece means for joining said pair of leg elements at the other end of said pair of leg elements, said cross piece means including means for pressing said device down to compress said nasolacrimal ducts.

7. The device of claim 6 including a pair of handles extending from opposite ends of said cross piece means.

8. The device of claim 7 wherein said device is made of material sufficiently elastic that squeezing said pair of handles together spreads apart said contact surfaces.

* * * * *